United States Patent [19]

Terk

[11] 4,178,345
[45] Dec. 11, 1979

[54] CUVETTE CARTRIDGE

[75] Inventor: Harold S. Terk, Richardson, Tex.

[73] Assignee: Abbott Laboratories, North Chicago, Ill.

[21] Appl. No.: 876,079

[22] Filed: Feb. 8, 1978

[51] Int. Cl.$^2$ .................. G01N 33/16; G01N 21/24
[52] U.S. Cl. .................................. 422/61; 422/55; 356/246; 435/287
[58] Field of Search .............. 23/259, 253 R, 230 R; 356/246; 195/127

[56] References Cited

U.S. PATENT DOCUMENTS

| | | | |
|---|---|---|---|
| 3,691,017 | 9/1972 | Brown et al. | 356/246 X |
| 3,718,439 | 2/1973 | Rosse et al. | 23/259 |
| 3,895,661 | 7/1975 | Praglin et al. | 23/259 X |
| 3,961,899 | 6/1976 | Trivedi et al. | 23/259 X |
| 4,013,368 | 3/1977 | Acker et al. | 356/246 |
| 4,040,786 | 8/1977 | Trivedi et al. | 23/259 X |
| 4,060,388 | 11/1977 | Rapp | 356/246 X |

Primary Examiner—R. E. Serwin
Attorney, Agent, or Firm—Merriam, Marshall and Bicknell

[57] ABSTRACT

A cuvette cartridge which is adapted for use with analyzer apparatus. The disposable, substantially rigid cartridge includes a chamber and a plurality of cuvettes disposed adjacent the chamber. The cartridge has no secondary air escape means. An opening is located between the chamber and each cuvette. The cartridge is preferably filled by a series of pressurizing operations in which pressure is exerted on fluid in the chamber and fluid from the chamber is forced into the cuvettes. The air pressure in the cuvettes and chamber is then equalized, after which the chamber is again pressurized and fluid is again forced into the cuvettes. The filling operation is repeated until the cuvettes are filled to the desired level. The cuvette filling operation occurs in essentially a closed system so that the air in the cuvettes is not permitted to escape during a filling operation.

5 Claims, 7 Drawing Figures

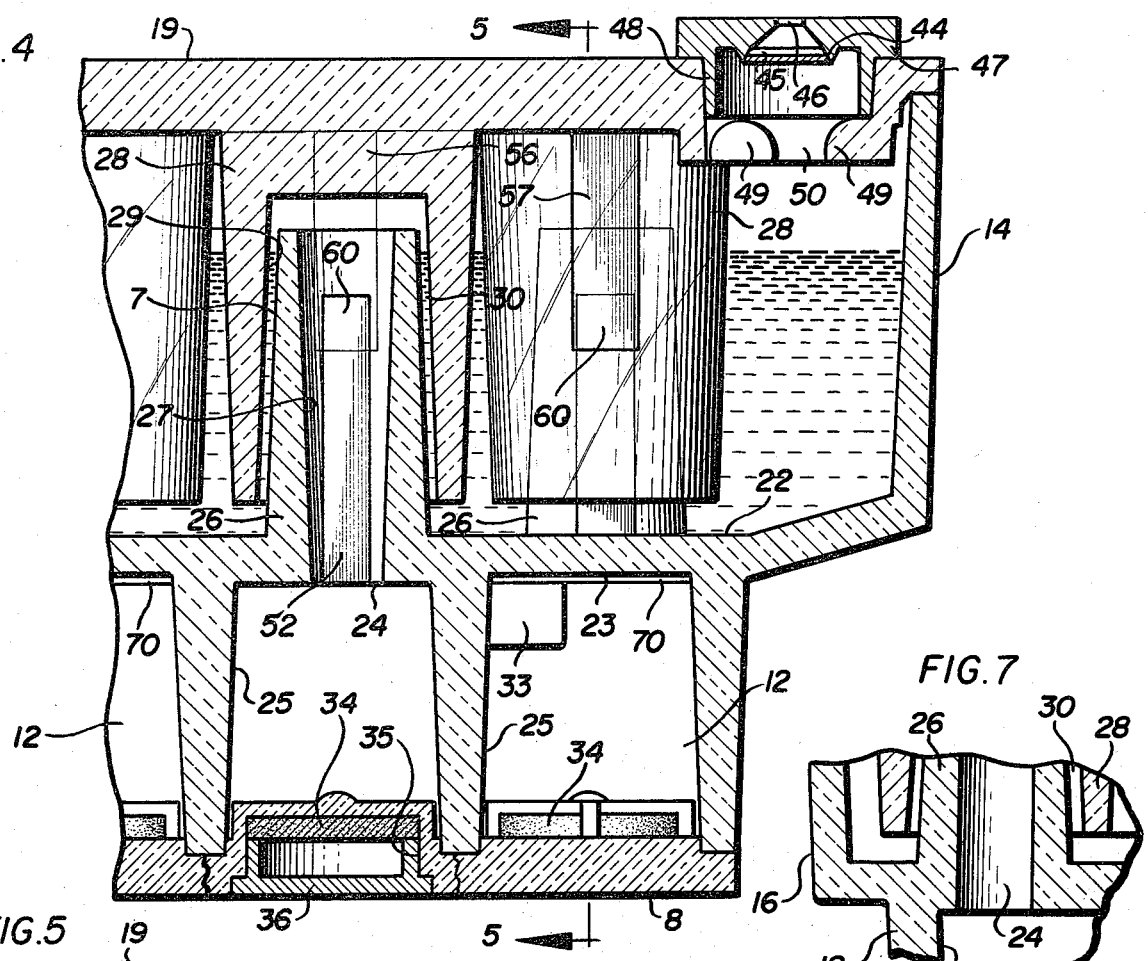
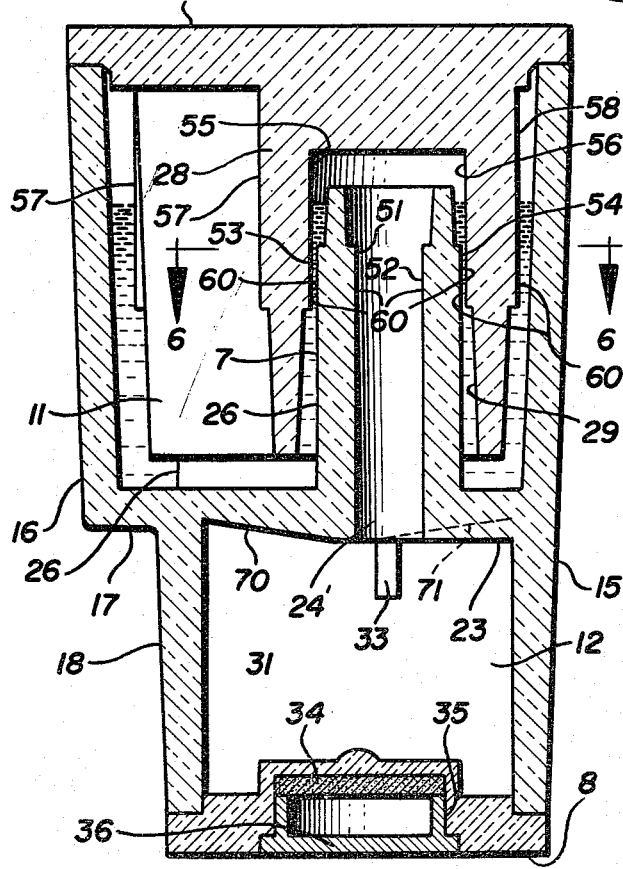
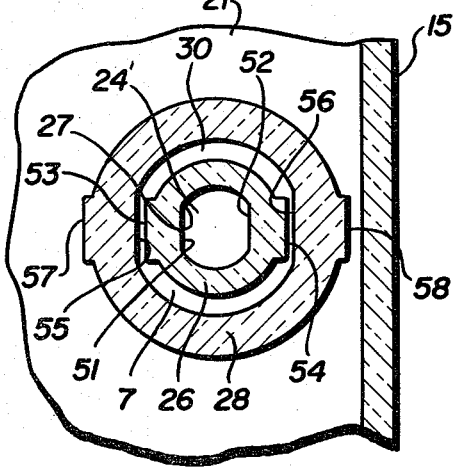

CUVETTE CARTRIDGE

BACKGROUND OF THE INVENTION

The present invention relates generally to a new and improved cuvette cartridge for use with a chemical and microbiological analysis apparatus and to a method of transferring biological or other fluid from a growth or filling chamber in the cartridge to a plurality of cuvettes.

Biological fluid analyzer apparatus, such as disclosed in U.S. Pat. No. Re. 28,800 and U.S. Pat. No. 3,718,439, are capable of performing antibiotic susceptibility testing, medical bacteriology procedures, clinical chemical analysis and other related procedures. When an evaluation is undertaken with this apparatus, a biological fluid to be evaluated, such as serum, plasma, urine, cerebrospinal fluid is inoculated into an artificially prepared nutrient or reagent fluid and placed into a cuvette cartridge of the type disclosed and claimed in Acker et al. U.S. Pat. No. 4,013,368. The prior art cartridge includes a growth chamber and a plurality of cuvettes disposed below the chamber. Fluid communication means are provided between the chamber and cuvettes to allow fluid to be transferred from the chamber to each of the cuvettes.

Impregnated paper discs or a lyophilized antibiotic agent or other desired reagent are located in the cuvettes.

The cartridge is placed in the analyzer apparatus, and a pressure or vacuum source is utilized to create a pressure differential sufficient to allow the fluid in the cartridge growth chamber to pass into each of the cuvettes. Gas in the cuvettes is evacuated through a gas pervious membrane.

Once the fluid is in the cuvettes, the antibiotic or reagent in the disc becomes rehydrated and forms an antibiotic and media/micro-organism suspension. The bacterial growth rate for the fluid in the various cuvettes can then be monitored by means of a plurality of individual optical detector systems, each of which is in registration with its respective cuvette.

Electronic computation means such as computers and/or other computing devices well known in the art, are available to evaluate the output of the detection system and to make appropriate calculations, either through analog or digital means, to record and display the results in a meaningful and appropriate manner. These results include, for example, the changes in the growth rate in each cuvette and the relative changes between the control cuvette containing no antibiotic and the sample cuvettes.

Unfortunately, cuvette cartridges presently employed with fluid analyzer apparatus available in the art are not entirely satisfactory for a number of reasons. Initially, cuvette cartridges presently known in the art are costly due to their particular physical structures, the relatively complex manufacturing procedures associated with making the cartridges and the quality control procedures required to assure the desired cartridge quality. These factors are all significant when it is considered that the cartridge is a disposable type device generally associated with a one time use.

For example, one cuvette cartridge known in the art and disclosed in U.S. Pat. No. 4,013,368 utilizes a resilient unidirectional valve and a gas permeable tubular member as part of its system for transporting fluid from a growth chamber to a plurality of cuvettes. This particular structure has not been entirely satisfactory because of the expense associated with the materials utilized to make the cartridge and because the gas permeable member is not always uniform in its structural characteristics along its length, a drawback which not only adversely affects gas removal from the system but also dictates increased quality control procedures.

Another cuvette cartridge which is known in the art is a membrane type cuvette cartridge. In this particular embodiment, a chamber, located above the cuvettes, is partitioned to form two compartments. One compartment serves as a fluid growth chamber while the remaining compartment serves as a vacuum compartment. A partition, which separates the upper chamber compartments from the lower cuvettes, has openings which serve as passages for biological fluid being evaluated and for gas which is evacuated from the cuvettes. A hydrophobic membrane strip is affixed to the top surface of the separating partition so that it covers the various openings in the bottom wall of one chamber compartment and a hydrophobic membrane strip also is affixed to the bottom wall in the remaining chamber compartment. In operation, air in the cuvette is evacuated from the cuvette into the vacuum compartment while the fluid is forced through the hydrophobic membrane strip into each of the cuvettes.

Problems, aside from manufacturing and quality control problems, exist with the membrane type cuvette cartridge. The membrane type cuvette cartridges presently available have been designed to substantially fill the cuvettes with fluid. However, various applications require that air be present in the cuvettes, inasmuch as many bacteria require oxygen for growth. Efforts to provide uniform air bubbles in the cuvettes of the membrane type cuvette cartridge have been unsuccessful. Because of the particular physical characteristics of the membrane at the location of the opening to each cuvette, the air flow through the membrane into each of the cuvettes varies substantially. As a result air will flow into one cuvette easier than it will flow into another cuvette due to the impedance caused by the structure of the membrane strip. The difference in impedance of the membrane at the various openings to each of the cuvettes causes non-uniform air bubbles in the cuvettes.

Another disadvantage that sometimes occurs with the utilization of the membrane strip is that the fluid located in the interstices of the membrane strip creates a hydraulic lock so that air cannot pass into the cuvettes. As a result, the bacteria in the fluid located in the cuvettes is starved of oxygen, thereby adversely affecting bacterial growth in the cuvette.

What is desired is a cuvette cartridge in which the individual cuvettes can be filled without the cost, assembly and quality control problems associated with cartridges presently available. Moreover, it is desired to have a cuvette cartridge in which the cuvettes are not completely filled, but instead have a relatively uniform amount of air available in each cuvette to permit proper growth of the bacteria when it is located in the cuvettes.

SUMMARY OF THE INVENTION

The invention disclosed and claimed herein serves to eliminate the problems associated with cuvette cartridges presently available. The cuvette cartridge of the present invention provides for a closed system in that there is no secondary air escape means. Therefore, the cuvettes can be partially and relatively uniformly filled so that air is available in the cuvettes to allow for proper growth of the bacterial fluid when it is located in the cuvettes. Moreover, the cartridge of the present invention can be readily made without the cost, manufacturing and quality control problems attendant with the membrane and unidirectional valve type cuvette cartridges.

Briefly, the cuvette cartridge of the present invention is adapted for use with analyzer apparatus presently available and disclosed, for example, in U.S. Pat. No. Re. 28,800. The cartridge preferably is membraneless, and the growth chamber need not be compartmentalized. While a number of embodiments can be utilized, one embodiment includes a cartridge comprising a growth chamber which is coextensive with and disposed above a plurality of cuvettes. The bottom wall of the growth chamber serves as the top wall for the cuvettes. An opening is located in this wall above each of the cuvettes. First members extend upwardly from this wall into the chamber at the location of each of the spaced openings. The first members are of a length which is less than the height of the growth chamber. Second members, which are slightly larger in internal diameter than the external diameter of the first members, extend downwardly from the roof or lid of the cartridge but stop short of the growth chamber floor. Each of the second members is axially aligned with and partially overlaps a respective first member to define a separate, annular, column-like passageway between the chamber and each cuvette.

In use, each cuvette is loaded with an antibiotic discs or lyophilized reagent which is inserted through a port or plug means located at the bottom of each cuvette. The upper growth chamber is filled with a particular fluid media through a filling port located in the lid or roof of the cartridge. Once the desired amount of fluid is placed in the growth chamber the filling port is closed with a plug having a gas permeable, liquid and bacteria impermeable membrane through which gas may pass into or out of the chamber. Preferably, the chamber is then suitably pressurized, with gas introduced through the membrane. The fluid media being incompressible will be forced up the various annular passageways formed by the first and second overlapped members where it will spill over the upwardly extending first members and pass downwardly therein and through the openings in the bottom wall of the growth chamber into the individual cuvettes, whereupon the individual cuvettes are filled with fluid. The fluid flow will continue until the pressure in the cuvettes has increased or equalized itself to the pressure in the upper growth chamber pursuant to Boyle's law relating to gases, i.e., $P_1V_1/T_1 = P_2V_2/T_2$. Thus when the gas pressure $P_1$ is increased to $P_2$, the volume of the gas will increase from an initial volume $V_1$ to a higher gas volume $V_2$ in the upper chamber while the reverse is occurring in the cuvettes which are being filled with fluid.

The cartridge of the present invention can be readily manufactured with the first and second members being integrally formed as part of the chamber roof and bottom wall, respectively. The quality control and assembly problems associated with the membrane style cartridge are obviated.

Further, the cuvette cartridge of the present invention has no secondary air vent means. It is what is referred to as a closed system except for the plugged, gas permeable, filling port in the growth chamber which permits the fluid to transfer to the cuvettes. In a pressurizing filling operation, air is not expelled from the cuvettes while they are being filled with fluid. Trapped air in the cuvettes is used to build up pressure as the system equalizes itself according to the pressure, volume formula for gases, i.e., $PV = K$.

The exit opening in the growth chamber for transfer of innoculated fluid from the growth chamber to the cuvette is below or at the same elevation as the final fluid level in the growth chamber while the entry opening in the cuvette for the biological fluid transfer is above the final fluid level in the cuvette.

BRIEF DESCRIPTION OF THE DRAWINGS

The invention together with its further objects and advantages thereof may be best understood by reference to the following description taken in conjunction with the accompanying drawings, in which like reference numerals identify like elements in the several figures and in which:

FIG. 4 shows a partial sectional view of the cuvette cartridge taken along line 4—4 in FIG. 2;

FIG. 5 shows a partial end sectional view taken along line 5—5 in FIG. 4;

FIG. 6 shows a partial sectional view taken along lines 6—6 in FIG. 5; and,

FIG. 7 shows a partial sectional view of a cuvette opening taken along lines 7—7 in FIG. 3.

DETAILED DESCRIPTION

Figure 1:
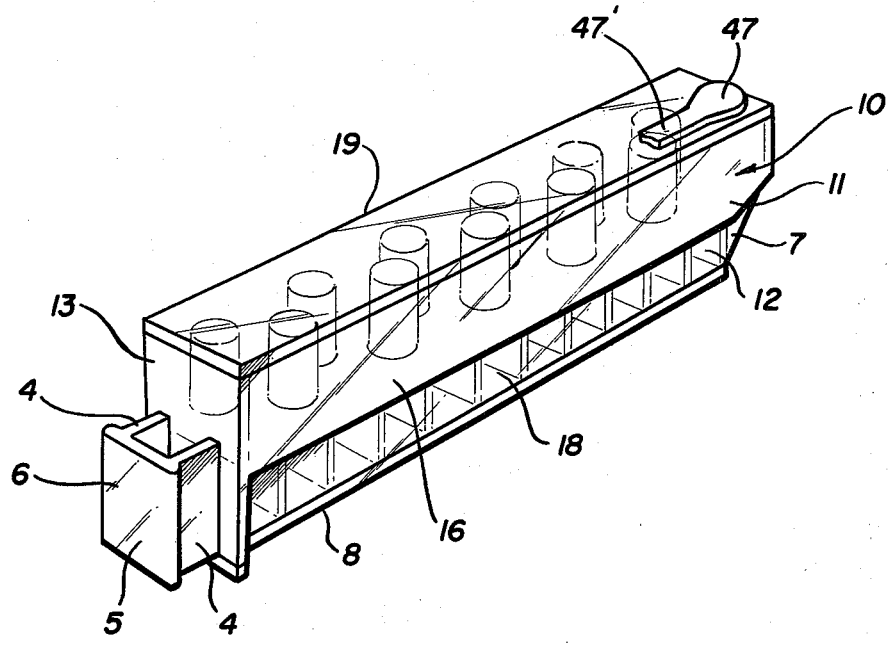
FIG. 1 shows a perspective view of an embodiment of the cuvette cartridge of the present invention.

Referring to the drawings, the disposable cuvette cartridge 10 of the present invention includes a growth chamber 11 which is positioned adjacently above and coextensive with a plurality of cuvettes 12.

Cartridge 10 includes spaced end walls 13, 14 which are joined to the respective ends of spaced side walls 15, 16. The bottom portion 18 of sidewall 16 is recessed inwardly at 17 as shown in FIG. 1 and 5 in order that the cartridge can be inserted into an analyzer apparatus. It is appreciated that the cartridge could have other physical configurations in order to fit with particular analyzer apparatus. The disposable cartridge further includes a bottom wall 8 and a top wall or lid 19. Gussett 2 serves to strengthen the cartridge at the end of the cartridge which extends beyond the cuvettes 12. Handle assembly 6 includes projections 4, which extend outwardly from endwall 13. Cross member 5 is joined to projections 4. When a cartridge is inserted in an analyzer apparatus, it can be picked up by handle assembly 6 and readily inserted into the cartridge receiving opening in an analyzer apparatus.

The cartridge can be manufactured from any suitable material including glass or a polymeric material such as a polyolefin, a polycarbonate or an acrylic. However, the material selected should provide a transparent cartridge having excellent chemical resistance properties and a satisfactory optical density for the particular application.

The cartridge can be made with lid 19 and bottom wall 8 molded separately from the remainder of the cartridge, after which the cartridge parts can be heat sealed together or otherwise joined in any suitable manner to form a leakfree, air tight cartridge.

Intermediate bottom wall 8 and lid 19 is a third wall 21. Wall 21 includes top surfaces 22 and bottom surface 23. Wall 21 is joined along its periphery to sidewalls 15, 16 and end walls 13, 14. A plurality of spaced openings 24 and 24' are located along the length of the wall 21. The openings serve as the exit for fluid from growth chamber 11 and the entrance for fluid into each cuvette 12.

Referring to FIGS. 1, 4 and 5, it will be seen that chamber 11 is located above wall 21 while a plurality of cuvettes 12 are located below wall 21. The cuvettes are separated from one another by means of spaced vertical walls 25 which extend from the bottom surface 23 of wall 21 to bottom wall 8. The cuvettes are positioned along the length of cartridge 10 so that at least one opening 24 or 24' is located above each cuvette 12.

A first short tubular member 26 is located at each opening 24 or 24' and extends upwardly from wall 21 for a portion of the height of chamber 11 as seen in FIG. 5. The outer surface of member 26 is tapered upwardly with the smallest external diameter being located at the top of the tube. Conversely, the internal surface 27 of member 26 is tapered downwardly with the largest internal diameter being located at the top of tubular member 26 while the smallest internal diameter is located at the bottom of tubular member 26, at opening 24 or 24'.

A plurality of second tubular members 28 are joined to and depend from lid 19. Tubular members 28 are internally tapered at 29 to correspond to the tapered external wall of members 26 and have a length which is less than the height of chamber 11. They are positioned on lid 19 so that when lid 19 is placed on cartridge 10, tubular members 28 overlap and fit concentrically over first tubular members 26. Tubular member 28 has a larger internal diameter than the external diameter of tubular member 26 so that an annular fluid passageway 30 is formed between the overlapped tubular members 26, 28.

Accordingly, when an innoculated fluid or medium is passed from chamber 11 to cuvettes 12, the fluid initially travels up the annular column 30 formed by tubular members 26 and 28. The fluid then passes downwardly inside tubular members 26 and exits from chamber 11 through openings 24 and 24' into cuvettes 12.

Tubular members 26, 28 preferably are positioned in a staggered or offset relationship to one another along the length of cartridge 10. The staggered alignment allows for more uniform mixing of the fluid growth medium in chamber 11 when the cartridge is agitated in the instrument or apparatus prior to analysis.

Figure 2:
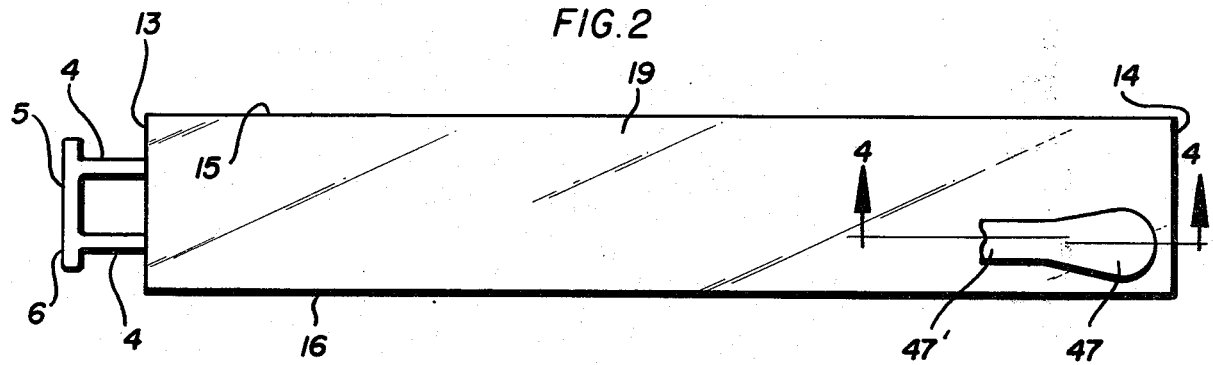
FIG. 2 shows a top view of the cuvette cartridge of FIG. 1.
Figure 3:
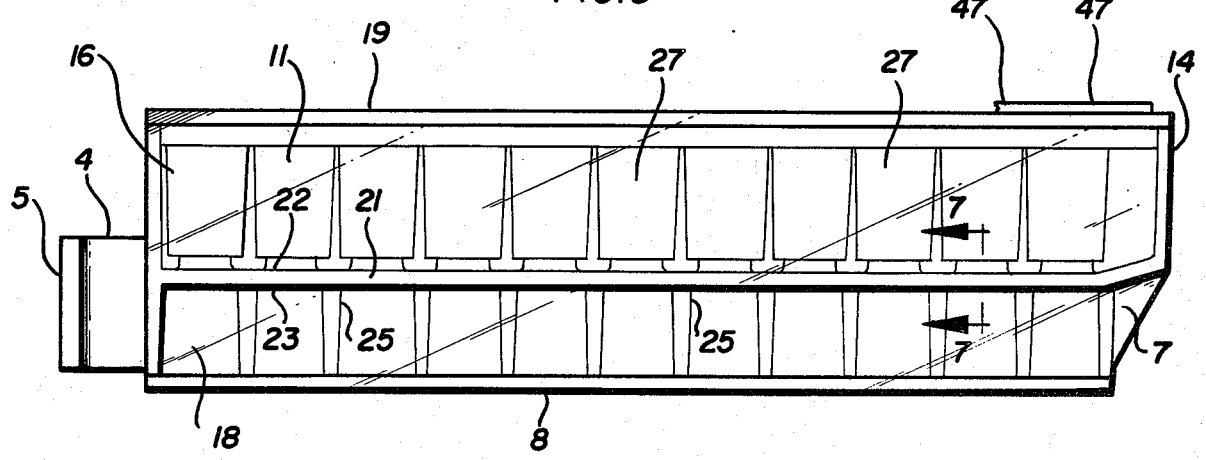
FIG. 3 shows a side view of the cuvette cartridge of FIG. 1.

Because of the staggered position of the tubular members, openings 24, 24' are likewise staggered or offset from each other. As a result, certain openings 24' in wall 21 are located intermediate cuvette sidewalls 15 and 18, as seen in FIGS. 2 and 5, whereas other openings 24 are located contiguous to wall 18. When fluid passes through those openings 24 which are located contiguous to sidewall 18, the fluid will run down the internal surface 31 of wall 18. However, when fluid flows from those openings 24' positioned intermediate sidewalls 15 and 17, a drop of fluid will, in some instances, be retained in opening 24' because of the tendency for the fluid to remain attached to the surface surrounding opening 24' due to surface tension.

The retained fluid droplets can be made to pass into the appropriate cuvette 12 by the inclusion of a tab or wick 33, FIGS. 4 and 5, which projects downwardly from bottom surface 23 of wall 21. Tab 33 is located adjacent opening 24' so that fluid will pass from opening 24' to tab 33 and down into cuvette 12.

Discs 34, which are impregnated to various concentrations with lyophilized antibiotic or other chemical reagents under evalutation, are inserted into relieved interior disc holder sections 35 of bottom wall 8. A hollow plug 36 encloses each disc 34 within its interior section 35, the plug being suitably retained in the interior section to complete a fluid and air tight seal between the plug 36 and section 35.

Referring to FIG. 4, cartridge lid 19 has an opening 50 formed in lid 19 for introducing an innoculated liquid medium to be evaluated. Spaced spherical members or bosses 49 project outwardly from the tapered wall 48 which forms opening 50. While only two members are shown, it is appreciated that the number of projections can vary. When chamber 11 is to be filled with fluid, the end of a pipette holding the fluid can be placed in opening 50 and seated against spherical members 48. Fluid can then be let into chamber 11 and air in the chamber will be evacuated out opening 50 in the annular space formed by wall 48 and the external wall of the pipette.

Once the innoculated fluid has been placed in growth chamber 11, opening 50 can be closed by inserting therein a press fit type plug 47 or other suitable closure means to prevent fluid in chamber 11 from leaking or otherwise passing out of the opening. As seen more clearly in FIG. 4, plug 47 includes a small opening 46 and a gas permeable, liquid and bacteria impermeable membrane 45 disposed below opening 46. Preferably, membrane 45 is seated in a flanged recess 44 of plug 47. Plug 47 is shown with a handle portion 47' which aids in inserting and removing the plug from opening 50. It is appreciated that other plug embodiments can be employed to close the opening 50.

In some applications, it is desired to make optical measurements of the fluid in growth chamber 11. However, the circular shapes of the tubular members 26, 28 do not provide the best optical surfaces. Therefore, to facilitate optical measurements, one or more pairs of mating tubular members 26 and 28 may be molded to provide a series of flat optical surfaces, as shown in FIGS. 5 and 6. Specifically, member 26 is molded to provide flat surface portions 51, 52 on internal wall surface 27 and flat surface portions 53, 54 on the outer wall surface 7 of member 26. Additionally, flat surface portions 55, 56 are molded on the internal surface 29 of tubular member 28 and flat surface portions 57, 58 are molded on the outer surface of member 28. The flat surface portions 51-58 on members 26 and 28 are molded so that they will all be aligned when member 28 is overlapped with member 26 as seen in FIGS. 4-6. The flat surface portion on each tubular member are of a sufficient length to allow the surfaces to overlap with each other at 60 (FIG. 4) to provide the desired optical characteristics.

Referring to FIGS. 4 and 5, it will be observed that, in each cuvette, a portion of lower surface 23 of wall 21 is inclined approximately 5°-10° to provide inclined cuvette roof sections 70, 71. The taper extends upwardly away from openings 24 and 24'. As a result, tapered section 70 in those cuvettes having openings 24' will taper upwardly away from opening 24' in one direction while the tapered section 71 in those cuvettes having openings 24 will taper upwardly away in the opposite direction (FIG. 5). While an inclined roof section has been shown, it is appreciated that other shapes, e.g. a dome shape, could be employed with the cuvettes.

OPERATION

In operation, a measured or desired amount of innoculated medium to be evaluated is placed in growth chamber 11 through opening 50. Plug 47 is then pressed in position to seal opening 50. The cartridge is inserted in an analyzer apparatus such as disclosed in Acker U.S. Pat. No. Re. 28,800 where it is innoculated and heated to increase the pressure in the cuvettes, thus serving to preclude premature transfer of the fluid from the growth chamber to the cuvettes.

A pressure source is attached to the cartridge at plug 47. Chamber 11 is then pressurized by a gas such as air which passes through gas permeable membrane 45. The increased gas pressure forces the fluid in chamber 11 up annular columns 30 and then down through tubular members 26. The fluid exits from chamber 11 through openings 24 and 24' into cuvettes 12.

The pressure normally available in the system, is not sufficient to transfer all the fluid from chamber 11 into cuvettes 12 in one cycle or operation. Accordingly, it is necessary to transfer the fluid from chamber 11 to cuvettes 12 in a series of pressurizing cycles until the desired volume of fluid has been obtained in each of the cuvettes 12.

As the pressure is increased in the growth chamber during a pressurizing cycle, the fluid in chamber 11, being incompressible, flows through the openings 24 and 24' to the various cuvettes until the pressure in the cuvettes has increased or equalized itself to the pressure in the upper chamber pursuant to Boyle's law relating to gases, i.e., $PV=K$, the temperature in the system being substantially constant. Accordingly, when the gas pressure $P_1$ is increased to $P_2$ in the growth chamber, the volume of the gas in chamber 11 will increase as the fluid is forced into the ventless cuvettes 12. Similarly, as the volume is reduced in cuvettes 12 as fluid enters the cuvettes, the gas pressure in the ventless cuvettes increases until equilibrium of pressure exists throughout the cartridge.

The cuvettes are filled to the desired volume for the particular application. There must be sufficient fluid in each of the cuvettes to permit the micro-organism evaluation.

In order to assure that presence of oxygen in the cuvettes is sufficient to allow the growth of the micro-organisms, an air space is created in each cuvette. This is accomplished by the provision of the inclined roof sections 70, 71.

The utilization of the cartridge of the present invention with its closed system for retaining air in the cuvettes also servies to provide an air lock, whereby fluid in the cuvettes will not travel or return to the growth chamber in the event the cartridge is inadvertently tipped or jostled. Inasmuch as the gas pressure in the cartridge is constant after the cuvette filling operation, the fluid is unable to return to growth chamber 11 because the air in the system after a filling operation will not be displaced.

If desired, a vacuum source can be applied to the cartridge after it is placed in the analyzer machine. The vacuum causes fluid to exit from cuvettes 12 to chamber 11 as air is pulled from the various cuvettes. The vacuum source may be located within the analyzer apparatus.

While one embodiment of the cuvette cartridge of the present invention has been shown, it is appreciated that it would be obvious to one skilled in the art to modify the cartridge. What is important is that the cartridge be closed in that no secondary air escape means are present so that air escapes from the cartridge during a pressurizing cuvette filling operation. Moreover, the exit openings in the growth chamber, for the transfer of biological fluid from growth chamber 11 to cuvettes 12, should be below or at the same elevation as the final fluid level in the growth chamber and the entry openings in the cuvettes should be located above the final fluid level in cuvettes 12. Accordingly, it is contemplated that the cartridge could have the cuvettes located on top of the growth chamber with concentrically fitting members 26 and 28 being replaced by a single tubular member open at both ends and molded to wall 21. One tube would be utilized with each cuvette. The tube would be open throughout its length and would project downwardly to just above the floor of the growth chamber and upward to just below the ceiling of the cuvette. This would provide a cartridge in which the exit in the growth chamber was below or at the same elevation as the final fluid level in the growth chamber and in which the entry opening in the cuvettes would be above the height of the final fluid level in the cuvettes.

Other cartridge embodiments could also be employed. It is contemplated that the tubular members 26 and 28 could be eliminated. The fluid would travel through openings 24 and 24' during a pressurizing cuvette filling operation. Further, with the closed system of the cartridge of the present invention, openings 24, 24' could employ a membrane strip across them to serve as a barrier for fluid in chamber 11 from inadvertently entering cuvettes 12.

While the cuvette cartridge of the present invention has been shown employing an overlapping tubular arrangement for each cuvette, it is appreciated that multiple cuvettes could be employed which do not employ a tubular arrangement for each cuvette. For example, if the cuvette cartridge was circular in shape, the cuvettes could be compartmentalized into pie-shaped sections. A singular tubular arrangement could be located in the chamber at the center of the cartridge with the exit opening from the chamber serving as an entrance opening for each of the cuvette pie-shaped sections.

The foregoing detailed description has been given for clearness of understanding only, and no unnecessary limitations should be understood therefrom, as modifications will be obvious to those skilled in the art.

What is claimed is:

1. A substantially rigid cuvette cartridge adapted for use with chemical and microbiological analysis apparatus, said cartridge comprising the following elements:
    a cartridge having a chamber with an opening for receiving fluid to be analyzed and a floor portion;
    a plurality of cuvettes in fluid communication with said chamber and extending in a given direction from said floor portion;
    a first fluid passage means extending in a direction opposite said given direction;
    a second fluid passage means extending in said given direction said first and second fluid passage means resulting in said fluid communication between said chamber and cuvettes.

2. A cuvette cartridge in accordance with claim 1 wherein said first and second fluid passage means overlap forming an annular column between the external wall surface of first fluid passage means and the internal wall surface of said second fluid passage means.

3. A cuvette cartridge in accordance with claim 1 wherein said chamber is positioned adjacently above said cuvettes.

4. A cuvette cartridge in accordance with claim 3 wherein said first and second passage means are tubular shaped.

5. A substantially rigid cuvette cartridge adapted for use with chemical and microbiological analysis apparatus, said cartridge comprising the following elements:

a chamber having an opening for receiving fluid to by analyzed;

a plurality of cuvettes disposed beneath said chamber; and paired concentric tubular members, the larger extending downward from the top of said chamber to a position above the bottom of said chamber and the smaller extending upward from the top of said cuvettes to a position below the top of said chamber, said concentric tubular members forming passageways between said chamber and cuvettes whereby pressure applied to the opening of said chamber will cause the fluid to be transferred from said chamber through the passageways and into the cuvettes for analysis.

* * * * *